(12) United States Patent
Britton et al.

(10) Patent No.: US 11,028,141 B2
(45) Date of Patent: Jun. 8, 2021

(54) THERAPEUTIC FOR THE PREVENTION AND/OR TREATMENT OF WEIGHT GAIN AND/OR DIABETES

(71) Applicant: Baylor College of Medicine, Houston, TX (US)

(72) Inventors: Robert Allen Britton, Houston, TX (US); Catherine Tomaro-Duchesneau, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 16/348,443

(22) PCT Filed: Nov. 9, 2017

(86) PCT No.: PCT/US2017/060809
§ 371 (c)(1),
(2) Date: May 8, 2019

(87) PCT Pub. No.: WO2018/089602
PCT Pub. Date: May 17, 2018

(65) Prior Publication Data
US 2019/0270790 A1    Sep. 5, 2019

Related U.S. Application Data

(60) Provisional application No. 62/419,581, filed on Nov. 9, 2016.

(51) Int. Cl.
| | |
|---|---|
| *A61K 38/16* | (2006.01) |
| *A61K 38/00* | (2006.01) |
| *A61P 1/00* | (2006.01) |
| *A61P 3/04* | (2006.01) |
| *C07K 14/605* | (2006.01) |

(52) U.S. Cl.
CPC ............ *C07K 14/605* (2013.01); *A61K 38/16* (2013.01); *A61P 1/00* (2018.01); *A61P 3/04* (2018.01); *A61K 38/00* (2013.01)

(58) Field of Classification Search
CPC . A61K 38/00; A61K 38/16; A61P 1/00; A61P 3/04; C07K 14/605
USPC ........... 530/308, 324; 514/7.2, 6.9, 1.1, 21.3
See application file for complete search history.

(56) References Cited

U.S. PATENT DOCUMENTS

| | | | | |
|---|---|---|---|---|
| 2002/0146701 A1* | 10/2002 | Hamilton | ......... | C07K 14/43595 435/6.16 |
| 2010/0166708 A1* | 7/2010 | Gallo | ...................... | A61P 33/00 424/93.2 |
| 2011/0268757 A1 | 11/2011 | Borras Cuesta et al. | | |
| 2011/0268787 A1 | 11/2011 | Bollag et al. | | |

FOREIGN PATENT DOCUMENTS

| | | |
|---|---|---|
| WO | 2008/103751 A2 | 8/2008 |
| WO | 2010/063865 A1 | 6/2010 |

OTHER PUBLICATIONS

Q79MA7 from UniProtKB, pp. 1-5. Integratedin to UniProtKB/TrEMBL on Jul. 5, 2004. (Year: 2004).*
Obesity from Merck Manual, pp. 1-13. Accessed Jun. 2, 2020. (Year: 2020).*
Diabetes Mellitus (DM) from Merck Manual, pp. 1-14. Accessed Jun. 2, 2020. (Year: 2020).*
Metabolic Syndrome from Merck Manual, pp. 1-3. Accessed Jun. 2, 2020. (Year: 2020).*
Nonalcoholic Fatty Liver Disease (NAFLD) from Merck Manual, pp. 1-4. Accessed Jun. 2, 2020. (Year: 2020).*
Short Bowel Syndrome from Merck Manual, pp. 1-2. Accessed Jun. 2, 2020. (Year: 2020).*
Yampolsky et al, "The Exchangeability of Amino Acids in Proteins," Genetics, Aug. 2005, 170: 1459-1472 (Year: 2005).*
Betts et al, "Amino Acid properties and Consequences of Substitutions," Bioinformatics of Geneticists, 2003, John Wiley & Sons, Ltd., 289-316. (Year: 2003).*
Designing Custom Peptides from Sigma, pp. 1-2. (Year: 2004).*
Schinzel et al, The phosphate recongition site of *Escheria coli* maltodextrin phosphorylase, FEBS, 286 (1,2): 125-128. (Year: 1991).*
Voet et Voet, John Wiley & Sons, Inc., pp. 235-241. (Year: 1995).*
Ngo et al., "Computational Complexity," Protein Structure Prediction, and the Levinthal Paradox, The Protein Folding Problem and Tertiary Structure Prediction, K. Merc Jr. and S. Le Grand Edition, pp. 491-495. (Year: 1994).*
Berendsen HJC, "A Glimpse of the Holy Grail?" Science, 282: 642-643. (Year: 1998).*
Bradley et al, "Limits of Cooperativity in a Structurally Modular Protein: Response of the NOtch Ankyrin Domain to Analogous Alanine Substitutions in Each Repeat," J. Mol. Biol., 324: 373-386. (Year: 2002).*
Hogan et al. "Glucagon-like peptide-1 (GLP-1) and the regulation of human invariant natural killer T cells: lessons from obesity, diabetes and psoriasis", Diabetologia 54.11 (2011 ): 2745-2751.
Mittermayer et al. "Addressing unmet medical needs in type 2 diabetes: a narrative review of drugs under development", Current diabetes reviews 11.1 (2015): 17-31.
Cogen et al. "*Staphylococcus epidermidis* Antimicrobial d-Toxin (Phenol-Soluble Modulin-c) Cooperates with Host Antimicrobial Peptides to Kill Group A *Streptococcus*", PLoS ONE, Jan. 2010, vol. 5, Issue 1, e8557.
Sansom et al., "Ion channels formed by amphipathic helical peptides", Eur Biophys J (1991) 20:229-240.

\* cited by examiner

*Primary Examiner* — Julie Ha
(74) *Attorney, Agent, or Firm* — Norton Rose Fulbright US LLP

(57) ABSTRACT

Embodiments of the disclosure encompass compositions and methods for the treatment of medical conditions in which increases in GLP-1 are beneficial to an individual. In specific embodiments, the disclosure concerns certain peptides that are capable of inducing GLP-1 production in an individual with a medical condition, such as type II diabetes or obesity. In other cases, an individual is not obese or overweight but is provided the peptide in an effort to reduce weight from fat.

7 Claims, 15 Drawing Sheets

Specification includes a Sequence Listing.

SEQUENCE LISTING

```
<160> NUMBER OF SEQ ID NOS: 2

<210> SEQ ID NO 1
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 1

Met Ala Ala Asp Ile Ile Ser Thr Ile Gly Asp Leu Val Lys Trp Ile
1               5                   10                  15

Ile Asp Thr Val Asn Lys Phe Lys Lys
            20                  25

<210> SEQ ID NO 2
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 2

Met Ala Ala Asp Ile Ile Ser Thr Ile Gly Asp Leu Val Lys Trp Ile
1               5                   10                  15

Ile Asp Thr Val Asn Lys Phe Thr Lys Lys
            20                  25
```

THERAPEUTIC FOR THE PREVENTION AND/OR TREATMENT OF WEIGHT GAIN AND/OR DIABETES

The present application is a national phase application under 35 U.S.C. § 371 that claims priority to International Application No. PCT/US2017/060809, filed Nov. 9, 2017 which claims priority to U.S. Provisional Patent Application Ser. No. 62/419,581, filed Nov. 9, 2016, all of which are incorporated herein by reference in their entirety.

TECHNICAL FIELD

Embodiments of the disclosure include at least the fields of cell biology, endocrinology, molecular biology, biochemistry, and medicine.

BACKGROUND

Glucagon-like peptide-1 (GLP-1) is an incretin hormone produced by a subset of enteroendocrine cells in the gut epithelium. GLP-1 therapeutics have demonstrated therapeutic efficacy in managing metabolic diseases. The present work demonstrates that a peptide, termed GspA, can enhance GLP-1 secretion and provide beneficial therapeutic effects in the context of obesity and diabetes.

BRIEF SUMMARY

Embodiments of the disclosure regard methods and compositions that concern treatment and/or prevention of a medical condition in a mammal, including a human, dog, or cat, for example. In specific embodiments, the medical condition is one in which increases in the production of the hormone Glucagon-like peptide 1 (GLP-1) would be therapeutic or beneficial in any manner, including to ameliorate one of more symptoms of the medical condition. Increased production of GLP-1 increases insulin sensitivity, reduces glucose production in the liver, as well as suppresses appetite, among other effects, which are beneficial in the treatment of diabetes and/or obesity, for example. In particular cases, an effective amount of a composition is provided to an individual in need thereof wherein the composition increases production of GLP-1 in the individual, although in alternative cases the composition is therapeutic through a mechanism that does not involve an increase in GLP-1 production.

In particular embodiments, the disclosure concerns the prevention and/or treatment of weight gain; a state of being overweight; obesity; any type of diabetes, including at least type 2 diabetes; Metabolic syndrome; Non-alcoholic fatty liver disease (NAFLD); and/or short bowel syndrome, for example. An individual may be at risk for becoming overweight, is at risk for becoming obese, or is at risk for becoming pre-diabetic or diabetic, for example because of genetic predisposition and/or because of personal and/or family history and/or because of lifestyle choices.

Certain embodiments of the disclosure encompass the induction of GLP-1 production as a therapeutic or preventative composition for Type II diabetes mellitus and obesity in an individual. In cases wherein diabetes is treated, in specific cases the composition treats the diabetes disease and may or may not be utilized for secondary conditions associated with diabetes, such as diabetic ulcers, for example. In specific embodiments, the therapeutic or preventative composition reduces body mass, reduces adiposity, reduces glycemia, increases insulin sensitivity, reduces glucose production in the liver, suppresses appetite, improves beta cell mass in the pancreas (cells that produce insulin), and/or decreases fasting glucose levels in an individual.

In particular embodiments of the disclosure, a composition for treatment or prevention of a medical condition comprises MAADIISTIGDLVKWIIDTVNKFKK (SEQ ID NO:1)(which may be referred to as the GspA peptide, and it is produced from *S. epidermidis*, and common names used are Hld or delta-toxin) or a functionally active fragment or derivative thereof. Peptides comprising alterations in the peptide of SEQ ID NO:1, including amino acid substitutions, inversion, deletions, truncations, and additions are encompassed herein.

In particular embodiments, the present disclosure does or does not encompass the delivery of whole organisms that secrete a therapeutic peptide of the disclosure.

In one embodiment, there is a method of treating or preventing a medical condition in an individual having insufficient levels of glucagon-like peptide-1 (GLP-1), comprising the step of providing to the individual a therapeutically amount of a peptide comprising MAADIISTIGDLVKWIIDTVNKFKK (SEQ ID NO:1), or a functionally active fragment or derivative thereof. In specific embodiments, the medical condition is obesity, diabetes (including type II diabetes), being an undesirable weight, Metabolic syndrome, Non-alcoholic fatty liver disease (NAFLD), short bowel syndrome, or a combination thereof. In some cases, the individual is provided another therapy for the medical condition.

In certain embodiments of methods of the disclosure, the method may further comprise the step of determining the level of GLP-1 in the individual.

In some cases, a peptide of the disclosure consists essentially of or consists of the sequence of SEQ ID NO:1, and the peptide may or may not be a length in the range of 5-50 amino acids in length. In specific embodiments, a derivative of a peptide does not have an alteration in the underlined positions of SEQ ID NO:1 as follows: MAADIISTIGDLVKWIIDTVNKFKK. Derivatives may comprise, consist of, or consist essentially of a sequence that is at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% identical to the sequence in SEQ ID NO:1.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

The scope of the present application is not intended to be limited to the particular embodiments of the process, machine, manufacture, composition of matter, means, methods and steps described in the specification.

DETAILED DESCRIPTION

Figure 1:
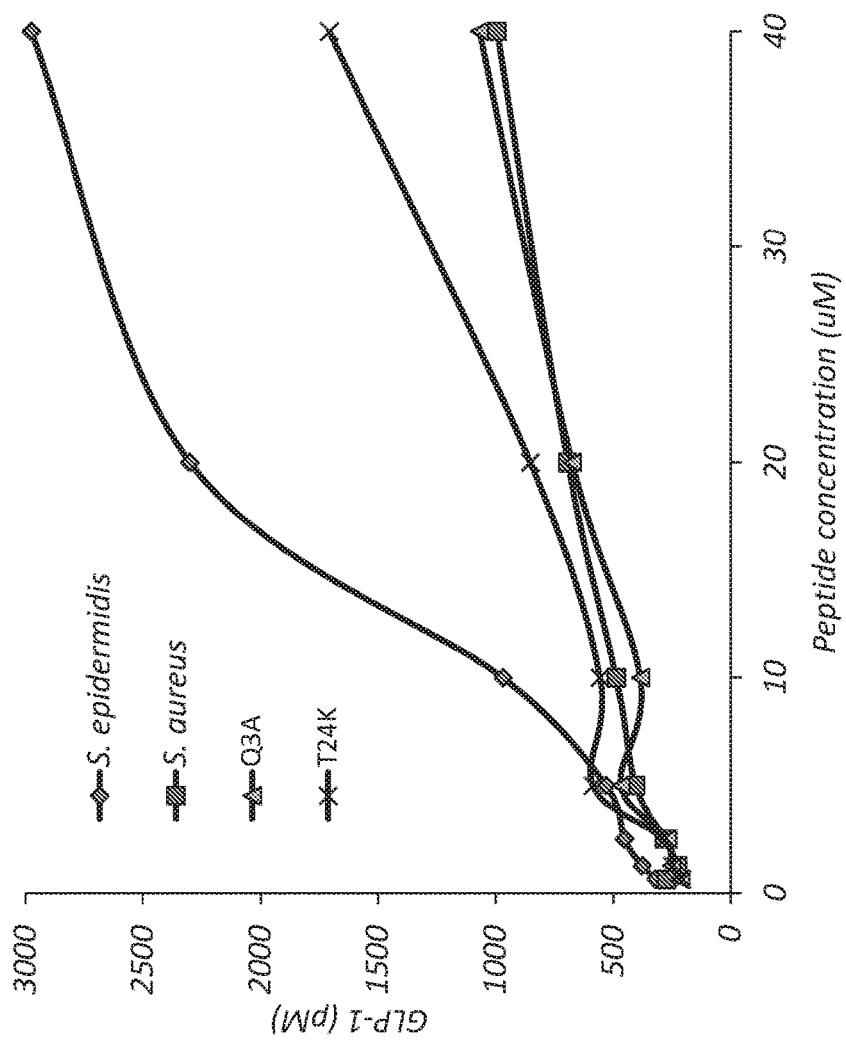
FIG. 1 shows GLP-1 stimulatory activity of GspA, *S. aureus* PsmD and the two mutants, Q3A and T24K at varying concentrations using NCI H716 cells. The data demonstrates that the GLP-1 stimulatory activity is specific to GspA.

As used herein the specification, "a" or "an" may mean one or more. As used herein in the claim(s), when used in conjunction with the word "comprising", the words "a" or "an" may mean one or more than one. As used herein "another" may mean at least a second or more. Still further, the terms "having", "including", "containing" and "comprising" are interchangeable and one of skill in the art is cognizant that these terms are open ended terms. Some embodiments of the disclosure may consist of or consist essentially of one or more elements, method steps, and/or methods of the disclosure. It is contemplated that any method or composition described herein can be implemented with respect to any other method or composition described herein.

As used herein, the term "effective amount" refers to an amount of a peptide comprising SEQ ID NO:1 (or functional fragments or derivatives thereof) that is required to improve at least one symptom of a medical condition in an individual; in specific embodiments, the medical condition exists in the individual directly or indirectly because of insufficient levels of GLP-1. In specific embodiments, the effective amount refers to the amount of peptide(s) that is utilized to increase GLP-1 levels in the individual.

In particular embodiments, this disclosure concerns the use of a small peptide for the treatment of medical conditions that would benefit from modulation of hormone secretion, such as increasing production of GLP-1, for example. In particular embodiments the medical condition comprises obesity (or the state of being overweight or the state of desiring a reduction in fat mass) and/or diabetes, including type 2 diabetes, for example. The peptide can mediate the release of the incretin hormone GLP-1 in cell culture, and in specific embodiments the peptide can suppress weight gain and decrease fasting glucose levels in mice on a high fat diet. The peptide may be formulated as a novel therapeutic for assisting mammals in maintaining a lean weight, in at least some cases. In particular cases, the peptide may be formulated to assist a mammal in preventing or reducing undesired weight gain in the form of an increase in adipose tissue (which may be referred to as adiposity) and/or preventing or slowing or reducing fat deposition and/or reducing glucose levels in the mammal.

I. Peptides of the Disclosure

In embodiments of the disclosure, one or more peptides are encompassed herein that modulate GLP-1 production, including at least increase GLP-1 production. In specific embodiments, the peptide comprises MAADIIS-TIGDLVKWIIDTVNKFKK (SEQ ID NO:1). In particular cases, a peptide comprising, consisting of, or consisting essentially of SEQ ID NO:1 is encompassed herein. The peptide may comprise part or all of the sequence of SEQ ID NO:1, and there may be additions and truncations of the peptide on the N-terminal and/or C-terminal end(s) of the peptide. In a specific case, there is an N-terminal addition and a C-terminal truncation compared to SEQ ID NO:1, and in other cases there is an N-terminal truncation and a C-terminal addition compared to SEQ ID NO:1. In cases wherein the peptide has an N-terminal and/or C-terminal extension, the peptide may be extended at the N-terminus and/or C-terminus by 1, 2, 3, 4, 5, 6, 7, 8, 9, 10, or more amino acids. In other cases, the peptide may lack one or more amino acids of SEQ ID NO:1, such as lack one or more amino acids of SEQ ID NO:1 from the N-terminus and/or C-terminus. In specific cases, the peptide lacks 1, 2, 3, 4, 5, 6, 7, 8, 9, 10, or more amino acids from the N-terminus and/or C-terminus of SEQ ID NO:1. An example of a variant is MAADIISTIGDLVKWIIDTVNKFTKK (SEQ ID NO:2).

In specific embodiments, there are one or more amino acid alterations compared to SEQ ID NO:1. There may be one alteration, two alterations, three alterations, and so forth compared to SEQ ID NO:1. The alteration may be an amino acid substitution and/or deletion and/or an inversion, compared to SEQ ID NO:1. Although in some cases any amino acid in the sequence of SEQ ID NO:1 may be altered, in other cases one or more amino acids are not able to be altered. In certain cases in an N-terminal to C-terminal direction of the peptide of SEQ ID NO:1, one or more amino acids at position 1, 2, 3, 4, 5, 6, 7, 8, 9, 10, 11, 12, 13, 14, 15, 16, 17, 18, 19, 20, 21, 22, 23, 24, or 25 are altered compared to SEQ ID NO:1. In specific cases, the amino acids underlined in the following sequence are not altered: MA<u>A</u>DIISTIGDLVKWIIDTVNKF<u>KK</u> (SEQ ID NO:1). In cases wherein an amino acid of the peptide is substituted, the substitution may or may not be with a conservative amino acid.

Thus, in certain embodiments there is a functionally active fragment or derivative of a peptide comprising, consisting of, or consisting essentially of SEQ ID NO:1. The fragments of the peptide may be at least or no longer than 5, 6, 7, 8, 9, 10, 11, 12, 13, 14, 15, 16, 17, 18, 19, 20, 21, 22, 23, 24, or 25 amino acids in length. The peptide length may be in a range at least or no more than 5-50, 5-40, 5-35, 5-30, 5-25, 5-24, 5-23, 5-22, 5-21, 5-20, 5-19, 5-18, 5-17, 5-16, 5-15, 5-14, 5-13, 5-12, 5-11, 5-10, 5-9, 5-8, 5-7, 5-6, 6-25, 6-24, 6-23, 6-22, 6-21, 6-20, 6-19, 6-18, 6-17, 6-16, 6-15, 6-14, 6-13, 6-12, 6-11, 6-10, 6-9, 6-8, 6-7, 7-25, 7-24, 7-23, 7-22, 7-21, 7-20, 7-19, 7-18, 7-17, 7-16, 7-15, 7-14, 7-13, 7-12, 7-11, 7-10, 7-9, 7-8, 9-25, 9-24, 9-23, 9-22, 9-21, 9-20, 9-19, 9-18, 9-17, 9-16, 9-15, 9-14, 9-13, 9-12, 9-11, 9-10, 10-25, 10-24, 10-23, 10-22, 10-21, 10-20, 10-19, 10-18, 10-17, 10-16, 10-15, 10-14, 10-13, 10-12, 10-11, 11-25, 11-24, 11-23, 11-22, 11-21, 11-20, 11-19, 11-18, 11-17, 11-16, 11-15, 11-14, 11-13, 11-12, 12-25, 12-24, 12-23, 12-22, 12-21, 12-20, 12-19, 12-18, 12-17, 12-16, 12-15, 12-14, 12-13, 13-25, 13-24, 13-23, 13-22, 13-21, 13-20, 13-19, 13-18, 13-17, 13-16, 13-15, 13-14, 14-25, 14-24, 14-23, 14-22, 14-21, 14-20, 14-19, 14-18, 14-17, 14-16, 14-15, 15-25, 15-24, 15-23, 15-22, 15-21, 15-20, 15-19, 15-18, 15-17, 15-16, 16-25, 16-24, 16-23, 16-22, 16-21, 16-20, 16-19, 16-18, 16-17, 17-25, 17-24, 17-23, 17-22, 17-21, 17-20, 17-19, 17-18, 18-25, 18-24, 18-23, 18-22, 18-21, 18-20, 18-19, 19-25, 19-24, 19-23, 19-22, 19-21, 19-20, 20-25, 20-24, 20-23, 20-22, 20-21, 21-25, 21-24, 21-23, 21-22, 22-25, 22-24, 22-23, 23-25, 23-24, or 24-25 amino acids in length. As used herein, the term "functionally active" refers to a peptide that when provided to an individual in a sufficient amount is able to increase GLP-1 level in that individual and/or is able to provide detectable improvement of at least one symptom of a medical condition. One or more ways to measure GLP-1 level to determine effectiveness of a particular peptide includes at least radioimmunoassay, ELISA, GLP-1 Receptor cell-line assays, Luminex, or a combination thereof, for example.

In some embodiments, a peptide derivative of SEQ ID NO:1 comprises sequence that is at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% identical to SEQ ID NO:1.

In specific embodiments, a peptide is modified such that it comprises one or more functional groups, such as with phosphorylation, glycosylation, carbonylation, myristoylation, isoprenylation, prenylation, palmitoylation, hydroxylation, and so forth.

In specific aspects, the peptide is biocompatible in which it produces no significant untoward effects when applied to, or administered to, a given organism according to the methods encompassed herein. The peptide may be purified from nature or it may be synthetically produced. Peptide compositions may be made by any technique known to those of skill in the art, including the expression of the peptide through standard molecular biological techniques, the isolation of the peptide from natural sources, or the chemical synthesis of the peptide. In some cases a mixture of peptides is employed, including in some cases a peptide comprising the sequence of SEQ ID NO:1 and another peptide with one or more alterations compared to SEQ ID NO:1.

In certain embodiments a peptide may be purified. Generally, "purified" will refer to a specific peptide composition that has been subjected to fractionation to remove various other proteins, polypeptides, or peptides, and which composition substantially retains its activity, as may be assessed, for example, by assays, as would be known to one of ordinary skill in the art for the specific peptide.

In specific embodiments, the peptide(s) is formulated as a pharmaceutical composition. Pharmaceutical compositions of the present disclosure comprise an effective amount of one or more peptides dissolved or dispersed in a pharmaceutically acceptable carrier. The phrases "pharmaceutical" and "pharmacologically acceptable" and used interchangeably herein refer to molecular entities and compositions that do not produce an adverse, allergic or other untoward reaction when administered to an animal, such as, for example, a human, as appropriate, and do not interfere with the therapeutic methods of the disclosure. The preparation of a pharmaceutical composition that contains at least one peptide or additional active ingredient will be known to those of skill in the art in light of the present disclosure, as exemplified by Remington: The Science and Practice of Pharmacy, 21 st Ed. Lippincott Williams and Wilkins, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The peptide(s) may comprise different types of carriers depending on whether it is to be administered in solid, liquid or aerosol form, and whether it needs to be sterile for such routes of administration, such as injection. The peptide(s) of the present disclosure can be administered intravenously, intradermally, transdermally, intrathecally, intraarterially, intraperitoneally, intranasally, intravaginally, intrarectally, topically, intramuscularly, subcutaneously, mucosally, intratumorally, orally, topically, locally, inhalation (e.g., aerosol inhalation), injection, infusion, continuous infusion, localized perfusion bathing target cells directly, via a catheter, via a lavage, in creams, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The peptide(s) may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present disclosure, the composition of the present disclosure suitable for administration may be provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a composition contained therein, its use in practicing the methods of the present disclosure is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present disclosure, the composition is combined with the carrier in any convenient and practical manner, i.e., by solution, suspension, emulsification, admixture, encapsulation, absorption and the like. Such procedures are routine for those skilled in the art.

In a specific embodiment of the present disclosure, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present disclosure may include the use of a pharmaceutical lipid vehicle compositions that incorporates a peptide, one or more lipids, and an aqueous solvent. As used herein, the term "lipid" will be defined to include any of a broad range of substances that is characteristically insoluble in water and extractable with an organic solvent. This broad class of compounds is well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present disclosure.

One of ordinary skill in the art would be familiar with the range of techniques that can be employed for dispersing a composition in a lipid vehicle. For example, the peptide may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present disclosure administered to the subject can be determined by physical and physiological factors such as body weight, severity of condition, the type of disease being treated, previous or concurrent therapeutic interventions, idiopathy of the subject and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% (by weight) of an active compound. In other embodiments, the active compound may comprise between about 2% to about 75% of the weight of the unit, or between about 25% to about 60%, for example, and any range derivable therein. Naturally, the amount of active compound(s) in each therapeutically useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration of the active agent, e.g., a peptide according to the present disclosure, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., of the active agent can be administered, based on the numbers described above.

Alimentary Compositions and Formulations

In particular embodiments of the present disclosure, the peptide(s) is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In one embodiment, the form of delivery is the use of bacteria, such as probiotic bacteria, engineered to produce and secrete the peptide(s) in situ in the gut.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration, the peptide compositions of the present disclosure may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively, the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10% (by weight), and preferably about 1% to about 2% (by weight).

Parenteral Compositions and Formulations

In further embodiments, the peptide(s) may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally.

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (see, e.g. U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

Miscellaneous Pharmaceutical Compositions and Formulations

In other preferred embodiments of the disclosure, the active compound peptide(s) may be slated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present disclosure may also comprise the use of a "patch". For example, the patch may supply one or more active substances at a predetermined rate and in a continuous manner over a fixed period of time.

In certain embodiments, the pharmaceutical peptide compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (see, e.g., Takenaga et al., 1998) and lysophosphatidyl-glycerol compounds (see, e.g., U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in, e.g., U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present disclosure for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

II. Methods of Use of the Peptide

Embodiments of the disclosure include methods and compositions for using any peptide(s) encompassed by the disclosure. In some cases, the peptide is utilized for decreasing weight in an individual in need of weight loss or is utilized for treating diabetes. The individual may be in need of a decrease in adipose mass, for example. The individual may be in need of weight loss for a variety of reasons, including because of a medical condition or state or for another reason. In cases wherein the individual is in need of weight loss because of a medical condition, the medical condition may or may not be a genetic condition and may or may not be an inherited condition. The cause of being in need of weight loss may be from genetics, metabolism, and/or illness. In specific embodiments, the medical condition encompasses being overweight or obese as a symptom. In some cases, the symptom of being overweight or obese is present in all individuals with the medical condition, although it may be present in less than all individuals with the medical condition. The symptom of being overweight or obese may be because of a defect in pathways related to adipose metabolic regulation, fat storage, and inflammatory processes, although in some cases being overweight or obese is not directly related to adipose metabolic regulation, fat storage, and inflammatory processes. The individual may be overweight or obese because of diabetes; hypothyroidism; metabolic disorders, including metabolic syndrome; medication side effects; alcoholism; eating disorder; insufficient sleep; limited physical exercise; sedentary lifestyle; poor nutrition; addiction cessation; and/or stress; although in some embodiments such conditions are the result of being overweight or obese.

In particular embodiments, an individual has a defect in GLP-1 control and is determined to be in need an improvement in such defect. In specific embodiments, the defect in GLP-1 control is that there is an insufficient amount of GLP-1 in an individual. In other cases the GLP-1 level is normal but the individual otherwise benefits from an increase in GLP-1 production. In particular embodiments, an individual has diabetes or is pre-diabetic and may or may not also be overweight or obese. The individual is provided an effective amount of one or more of any peptides of the disclosure to increase the production of GLP-1. Such treatment is provided to the diabetic or pre-diabetic individual and an improvement in the level of GLP-1 occurs. The increase in GLP-1 level may or may not be to normal GLP-1 levels. In particular embodiments, in addition to an improvement in GLP-1 production, one or more symptoms of diabetes or pre-diabetes is improved upon administration of one or more peptides of the disclosure. For pre-diabetic individuals, the onset of diabetes is prevented or delayed upon use of one or more peptides of the disclosure. In some cases, the severity of the medical condition is reduced upon administration of one or more of the peptides.

In specific embodiments, an individual in need of weight loss is overweight (BMI between 25 and 29) or obese (BMI of 30 or more). The individual that is subjected to methods and compositions of the disclosure may first be identified by a medical practitioner as being in need of weight loss, and the therapeutic composition may be delivered to the individual for the specific purpose of decreasing weight.

In one embodiment of the disclosure, there is a method of producing increased serum levels of GLP-1. The individual may be known to have a medical condition or physical state that would benefit from increased GLP-1 levels, or the individual may be suspected of having a medical condition or physical state that would benefit from increased GLP-1 levels. In particular embodiments, the individual subjected with methods and/or compositions of the invention desires prevention of one or more undesirable physical states (or the effects thereof, such as with diabetes or obesity) or medical conditions. In certain embodiments, an individual is provided effective levels of a particular peptide for the explicit purpose of increasing GLP-1 levels to treat, prevent, delay the onset of, or reduce the severity of a medical condition or physical state. In particular embodiments, an individual is identified as needing treatment (or prevention or delay of onset or reduction in severity) of a medical condition related to insufficient GLP-1 levels.

Embodiments of the disclosure concern a variety of methods for the treatment or prevention or delay of onset or reduction in severity of one or more medical conditions or physical state related to insufficient levels of GLP-1 in an individual. In specific embodiments are methods for the treatment or prevention or delay of onset or reduction in severity of one or more medical conditions or physical state related to insufficient concentrations of GLP-1. In specific aspects, methods allow for the treatment or prevention or delay of onset or reduction in severity of one or more medical conditions or physical states because of the benefits of increasing concentrations of GLP-1. In some cases, the level of GLP-1 in the individual is normal but an increase in the level of GLP-1 is therapeutic, whereas in other cases the level of GLP-1 in the individual is below normal and an increase in the level of GLP-1 (whether or not to normal levels) is therapeutic.

An individual in need thereof can include one that needs prevention or treatment of deleterious effects of obesity or that needs prevention or treatment of diabetes or complications from diabetes.

As used herein, the peptide may be utilized for diabetes, although it may or may not be utilized for a complication from diabetes, such as diabetic nephropathy, neuropathy, retinopathy, diabetic obesity, diabetic dyslipidemia, cardiometabolic syndrome, and combinations thereof, for example.

In certain embodiments of the disclosure, there are methods and compositions for the treatment of medical conditions caused directly or indirectly by insufficient GLP-1 levels in the individual. The individual may be of any age or state of health, although in particular embodiments the individual is elderly, is susceptible to particular medical conditions or physical states associated directly or indirectly with insufficient GLP-1 levels, or has a medical condition or physical state that is associated directly or indirectly with insufficient GLP-1 levels. The compositions delivered to the individual in such cases include at least a peptide encompassed by the disclosure, in particular acids to facilitate raising GLP-1 levels in the individual. One can measure GLP-1 levels using standard means in the art. In cases wherein an individual is treated for obesity, that individual may or may not be obese because of a genetic predisposition for obesity, because of lifestyle choices, or a combination thereof.

In specific embodiments, one or more medical conditions that are caused directly or indirectly by reduced levels of GLP-1 are treated or prevented with effective amounts of a peptide of the disclosure.

In specific embodiments, an individual is provided effective amounts of peptide compositions as described herein for the explicit purpose of raising levels of GLP-1 and because it is determined that the individual is afflicted with a condition for which such levels are directly or indirectly related. In specific cases, methods of the disclosure include the diagnosis of such medical condition(s).

In embodiments of the disclosure an individual is determined to be in need of weight loss, such as by measuring their weight and/or by measuring their BMI and/or having an MRI and/or DEXA scan for assessment of adipose mass. The individual may be known to be in need of weight loss or suspected of being in need of weight loss or at risk for being in need of weight loss. An individual may determine themselves that they are in need of weight loss and/or it may be determined by a suitable medical practitioner.

Once the individual is known to be in need of weight loss or known to be at risk or susceptible to being in need of weight loss, or in need of glucose control, they may be given a suitable and effective amount of a peptide encompassed by the disclosure. In specific embodiments, one or more peptides are provided to the individual, such as in a composition or in multiple compositions. A composition comprising a peptide may be specifically formulated for a therapeutic application.

An individual may be provided suitable dose(s) of peptide(s) on an as needed basis or as part of a routine regimen. The individual may also be taking other measures and/or compositions to lose weight or improve glucose levels in addition to taking the peptide(s). The individual may take the peptide(s) on a daily basis, weekly basis, monthly basis, and so on. The individual may take the peptide(s) with consumption of food or on an empty stomach.

The individual may or may not be monitored by a medical practitioner during the course of a peptide(s) regimen. The individual may cease to take the peptide(s) once a desirable weight is achieved or blood glucose levels are satisfactory without intervention and may resume taking the peptide(s) if the individual becomes in need of losing weight at a later point in time.

Effectiveness of a therapeutic may be measured by any suitable means, including MRI scans in a model or an individual to be treated to assess increase in adipose mass or measurements of body weight using a weighing scale, for example.

III. Combination Therapy

In some embodiments, the peptide treatment of the disclosure may precede, follow, or both another treatment by intervals ranging from minutes to weeks. In embodiments where the inventive composition(s) and the other agent are provided separately to an individual, one would generally ensure that a significant period of time did not expire between the time of each delivery, such that the inventive composition and the other agent would still be able to exert an advantageously combined effect on the individual. In such instances, it is contemplated that one may deliver both modalities within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Administration of the inventive compositions of the present disclosure to an individual will follow general protocols for the administration of drugs, taking into account the toxicity, if any, of the molecule. It is expected that the treatment cycles would be repeated as necessary. It also is contemplated that various standard therapies, as well as surgical intervention, may be applied in combination with the described therapy.

IV. Kits Comprising the Peptide(s)

Any of the peptide compositions described herein may be part of a kit. The kits may comprise a suitably aliquoted peptide of the present disclosure, and the component(s) of the kits may be packaged either in aqueous media or in lyophilized form. The container of the kits will generally include at least one vial, test tube, flask, bottle, syringe or other container, into which a component may be placed, and preferably, suitably aliquoted. Where there is more than one component in the kit, the kit also will generally contain a second, third or other additional container into which the additional component(s) may be separately placed. However, various combinations of components may be comprised in a vial. The kits of the present disclosure also will typically include container for holding the peptide and any other reagent containers in close confinement for commercial sale.

When the components of the kit are provided in one and/or more liquid solutions, the liquid solution is an aqueous solution, with a sterile aqueous solution being contemplated. The compositions may also be formulated into a syringeable composition. In which case, the container may itself be a syringe, pipette, and/or other such like apparatus, from which the formulation may be applied to a particular area of the body, injected into an individual, and/or even applied to and/or mixed with the other components of the kit. However, the component(s) of the kit may be provided as dried powder(s). When reagents and/or components are provided as a dry powder, the powder can be reconstituted by the addition of a suitable solvent. It is envisioned that the solvent may also be provided in another container.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

GSPA Peptide Studies

Studies in NCI H716 cells demonstrated that GspA alone is sufficient to enhance GLP-1 production. One can characterize the peptide and the mechanism(s) of GLP-1 modulation.

Studies identified strains of *S. epidermidis* with GLP-1 stimulatory activity on GLP-1 producing cells, the NCI H716 cells. *S. epidermidis* JA1 was demonstrated to have the highest GLP-1 stimulatory activity. Mass spectrometry analysis of the *S. epidermidis* supernatants identified GspA as a potential candidate for the observed GLP-1 stimulatory activity. GspA has sequence homology with a *S. aureus* peptide, termed delta toxin, with two amino acid changes. To test GLP-1 stimulatory activity, the GspA, *S. aureus* and mutant peptides (Q3A and T24K) were synthesized and incubated on NCI H716 cells at varying concentrations. Incubation of GspA on the NCI H716 cells led to a dose dependent release of GLP-1, with a release of 2980 pM of GLP-1 when incubated with 40 μm of GspA for 2 hours. Incubation with mutant forms of the peptide do not stimulate GLP-1 as well as GspA, nor does the *S. aureus* homolog of GspA. This data demonstrates an amino acid sequence specificity for GLP-1 stimulation (FIG. 1).

Figure 2:
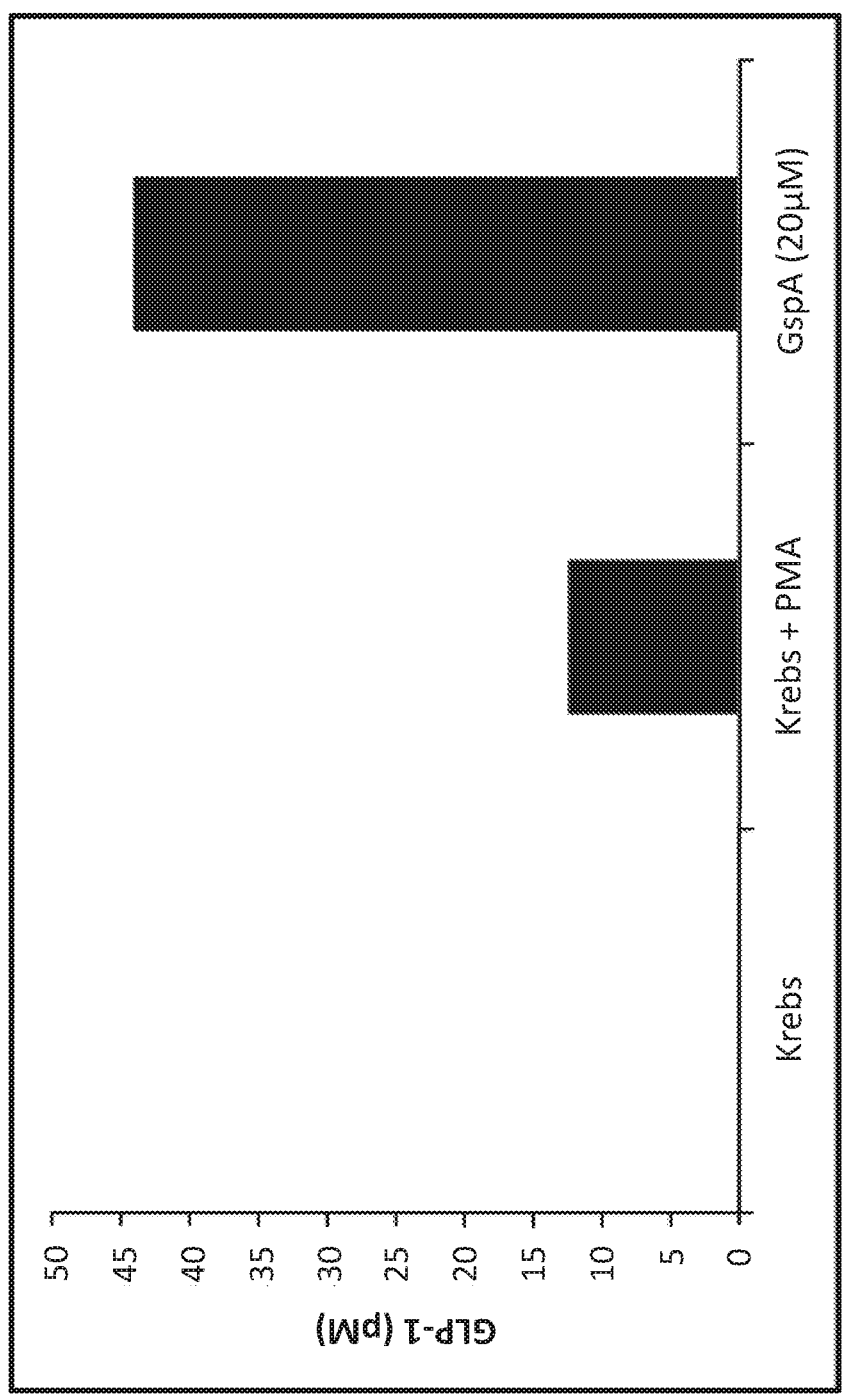
FIG. 2 shows results of a study using human intestinal enteroids that are engineered by Neurogenin-3 transduction to have increased levels of enteroendocrine cells secreting GLP-1. GspA (20 µM) was shown to stimulate GLP-1 release in this model. Krebs is the vehicle control and Krebs+PMA is a positive control (PMA is a positive control for the release of GLP-1). GLP-1 levels were measured by ELISA.

FIG. 2 provides results to confirm the GLP-1 stimulatory activity of GspA in a more relevant model than the transformed NCI H716 cells, human intestinal enteroids, often referred to as "mini guts." Human intestinal enteroids were engineered using Neurogenin-3 to have increased levels of enteroendocrine cells secreting GLP-1. As observed with NCI H716, GspA did stimulate GLP-1 release, approximately 45 pM following 2 hours of incubation with 20 μM of GspA.

Figure 3:
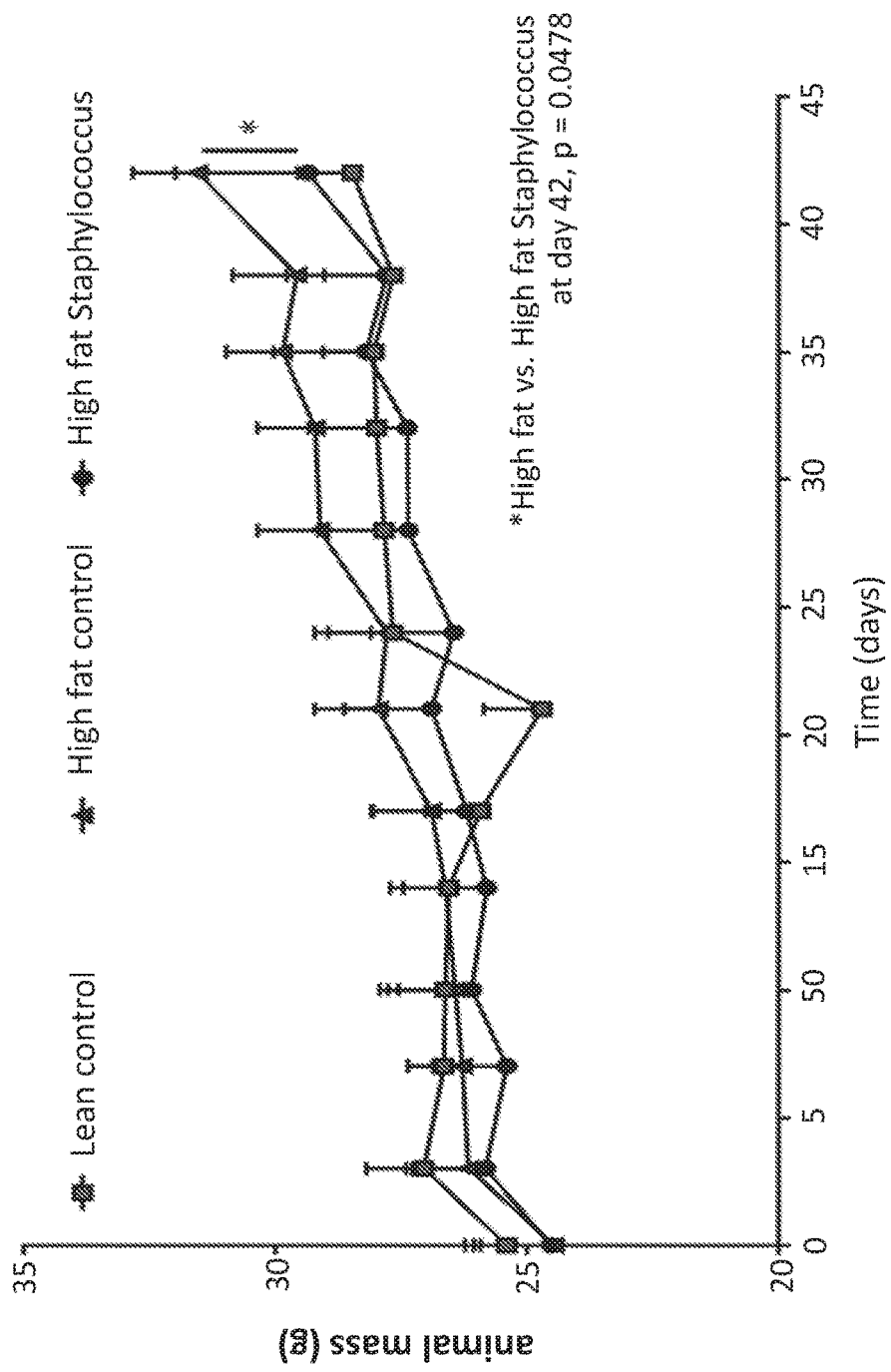
FIG. 3 shows that *S. epidermidis* that produces the GspA peptide reduces animal body mass over 42 days when provided to mice fed a high fat diet, compared to controls.
Figure 4:
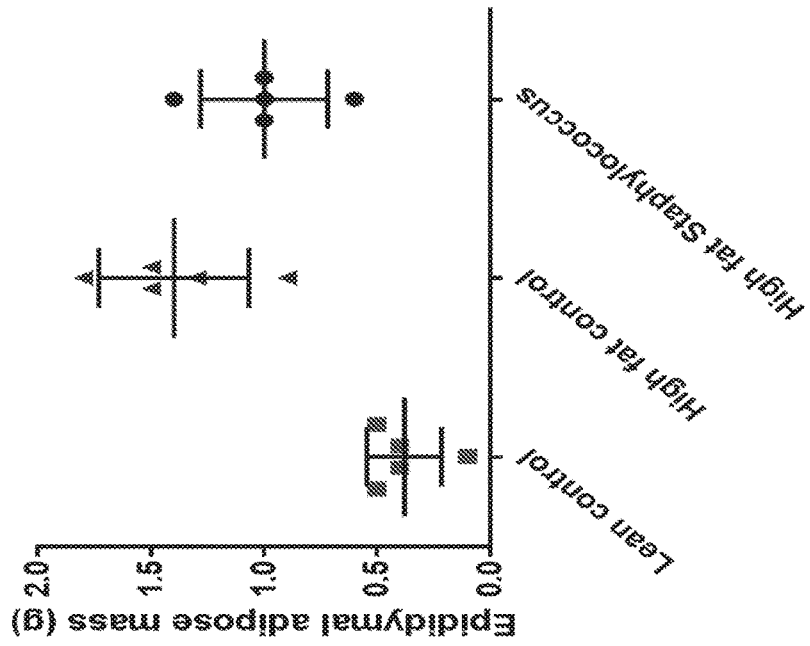
FIG. 4 demonstrates that *S. epidermidis* that produces the GspA peptide reduces adiposity, as measured by massing gonadal adipose tissue, in animals given a high fat diet, compared to controls.
Figure 4:
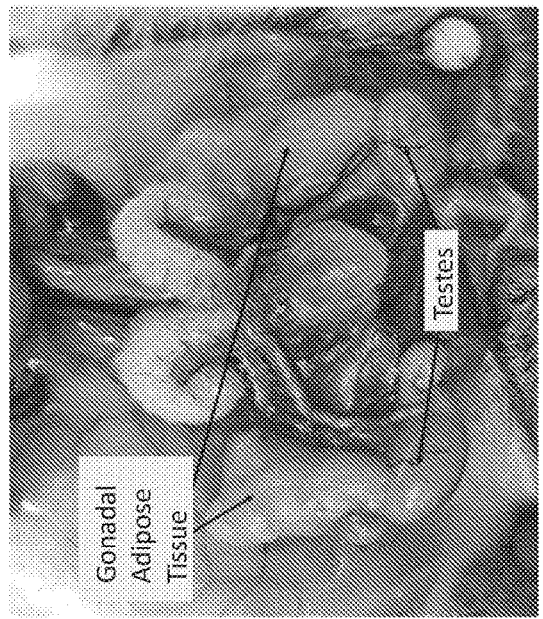
Figure 5:
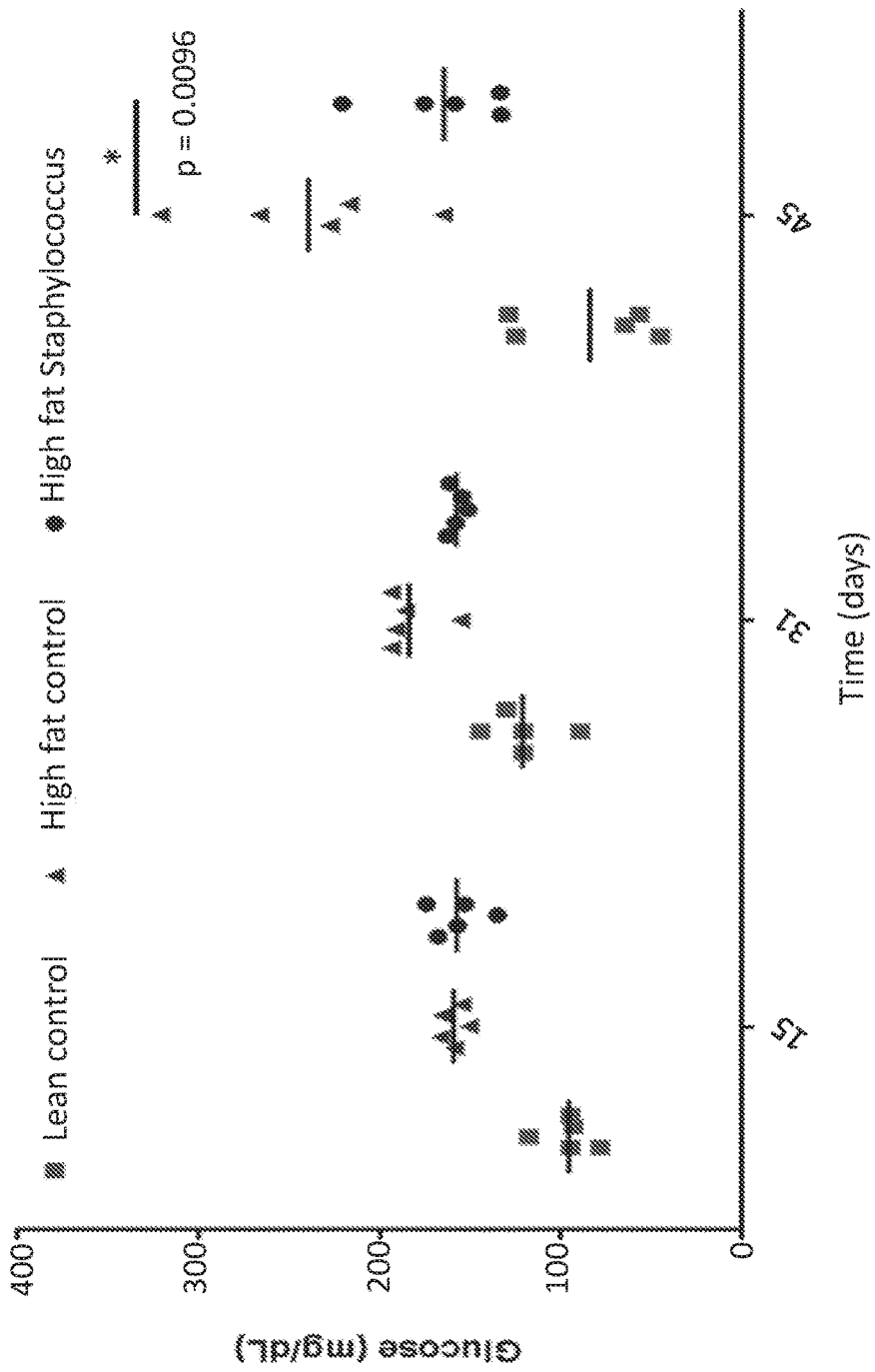
FIG. 5 shows that *S. epidermidis* that produces the GspA peptide reduces glycemia as measured by a glucose oxidase assay in high fat-fed animals compared to controls.

To investigate the effect of a GspA producing *S. epidermidis* (JA1) on metabolic disease, it was tested using a preliminary animal study in 8 week old male C57BL/6 humanized gut microbiota mice on a high fat diet, with administration of the GLP-1 stimulating *S. epidermidis* strain by oral gavage three times per week for 6 weeks. Briefly, there were three groups (n=5), with all mice fed ad libitum: 1) mice fed conventional chow administered GM17 bacterial culture media, 2) mice fed high-fat chow (60% lard) administered GM17, and 3) mice fed high-fat chow administered *S. epidermidis* ($5 \times 10^8$ cells/mouse). Animal mass was monitored every 3 days and 6 h fasting glucose levels every 2 weeks (FIGS. 3 and 4). There were statistically significant changes in animal mass at day 42 (p=0.0478) and fasting glucose at day 45 (p=0.0096), demonstrating an impact on both obesity and glycemia. Epididymal adipose tissue, weighed at sacrifice as an indicator of fat content (FIG. 5), demonstrated a decrease, although not statistically significant, in animals administered *S. epidermidis* compared to the untreated high-fat fed mice. Hence, an *S. epidermidis* strain capable of secreting GspA suppresses weight gain, adiposity, and hyperglycemia in mice.

Example 2

Therapeutic for the Prevention and/or Treatment of Weight Gain and/or Diabetes

Figure 6A:
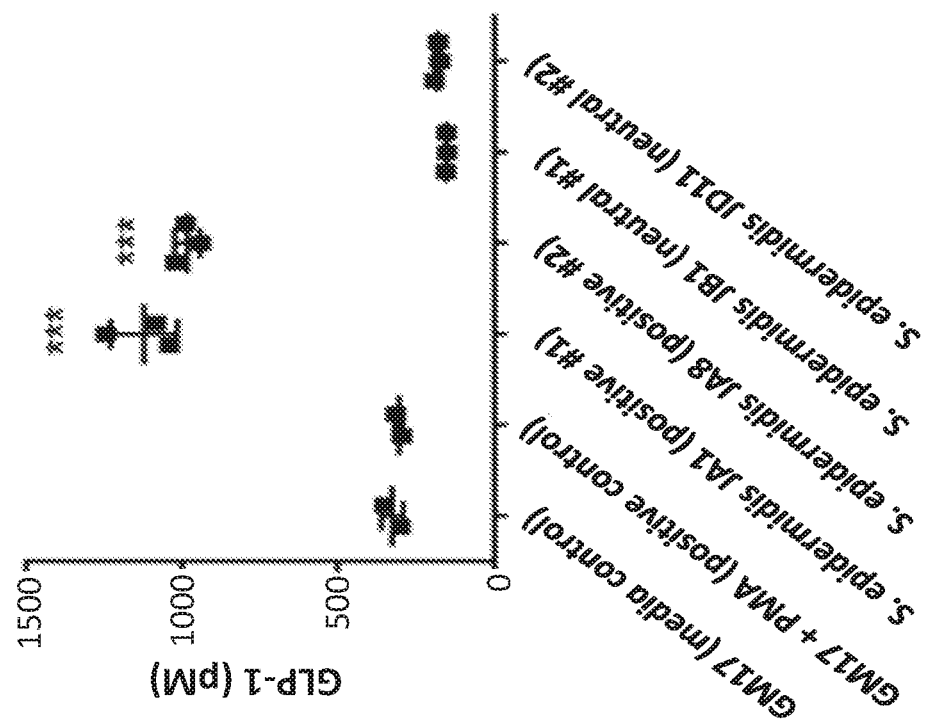
FIG. 6 shows glucagon-like peptide-1 levels are stimulated following exposure to cell-free *S. epidermidis* supernatants using (6A) NCI H716 and (6B) GLUTag cells, measured by ELISA. Effect of *S. epidermidis* supernatants on (6C) NCI H716 and (6D) GLUTag cell viability measured using a PrestoBlue resazurin-based assay.
Figure 6B:
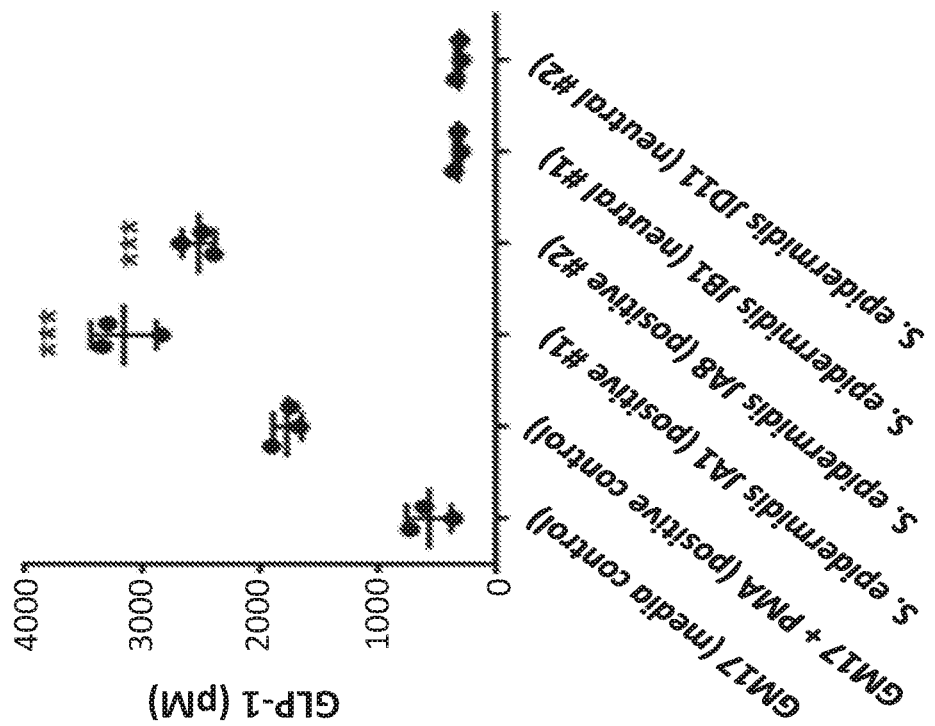
Figure 6C:
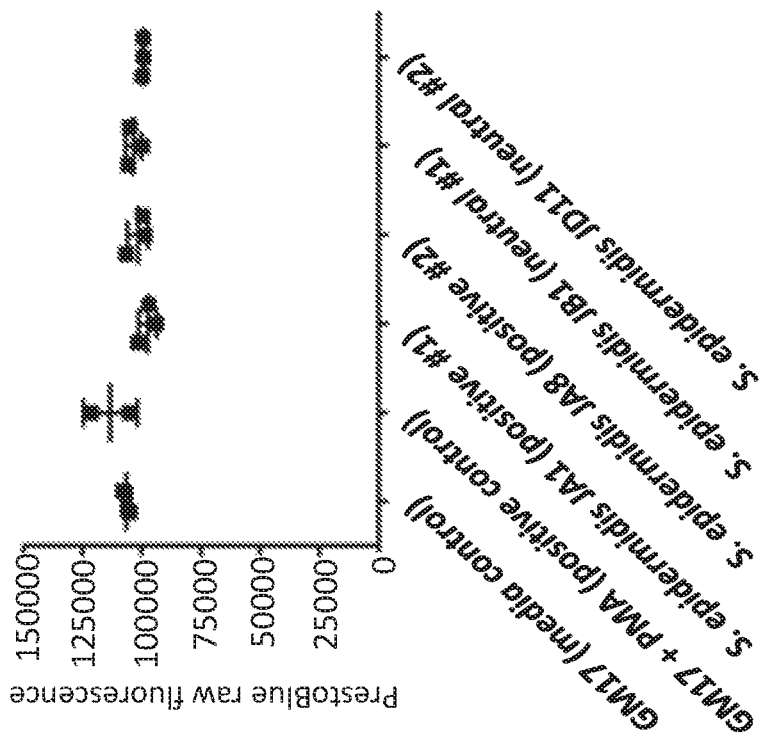
Figure 6D:
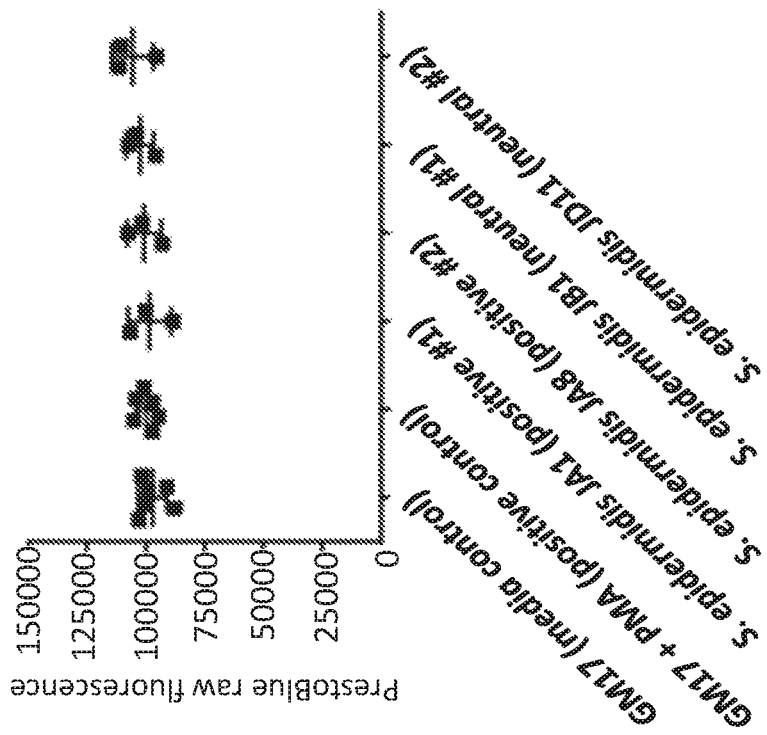

*S. epidermidis* has GLP-1 stimulatory activity in vitro in NCI H716 and GLUTag cells—In order to identify bacterial strains capable of eliciting GLP-1 secretion, 1500 microbial supernatants were screened using human NCI H716 cells. While the vast majority of strains had no impact on GLP-1 secretion, 45 isolates were identified that showed increased GLP-1 secretion above the positive PMA control. Following 16S rRNA sequencing, all 45 stimulatory strains came back as strains of *S. epidermidis*. Incubation of cell-free supernatants from two of the stimulatory strains with the highest activity, *S. epidermidis* JA1 and JA8 on NCI H716 cells stimulated a release of 3155±276 pM and 2518±141 pM GLP-1, respectively (FIG. 6A). GM17 media control and the PMA positive control had GLP-1 levels of 565±188 pM and 1767±120 pM GLP-1, respectively, indicating an approximate 2-fold increase in activity by JA1 over the positive PMA control. It was confirmed that JA1 and JA8 could stimulate GLP-1 secretion in a second model, murine GLUTag cells. *S. epidermidis* JA1 and JA8 led to the release of 1123±107 pM and 984±40 pM GLP-1, respectively (FIG. 6B). The GM17 media control and the PMA positive control had GLP-1 levels of 327±35 pM and 305±14 pM, respectively, indicating no real stimulation by PMA. Interestingly, strains of *S. epidermidis* without the ability to stimulate GLP-1 secretion, termed neutral, in both NCI H716 and GLUTag cells were also identified—strains JB1 and JD11. None of the *S. epidermidis* bacterial cell-free supernatants had detectable toxicity on NCI H716 (FIG. 6C) and GLUTag (FIG. 6D) cells, as determined by a PrestoBlue resazurin-based analysis which measures aerobic respiration as an indicator of cell viability.

Figure 7A:
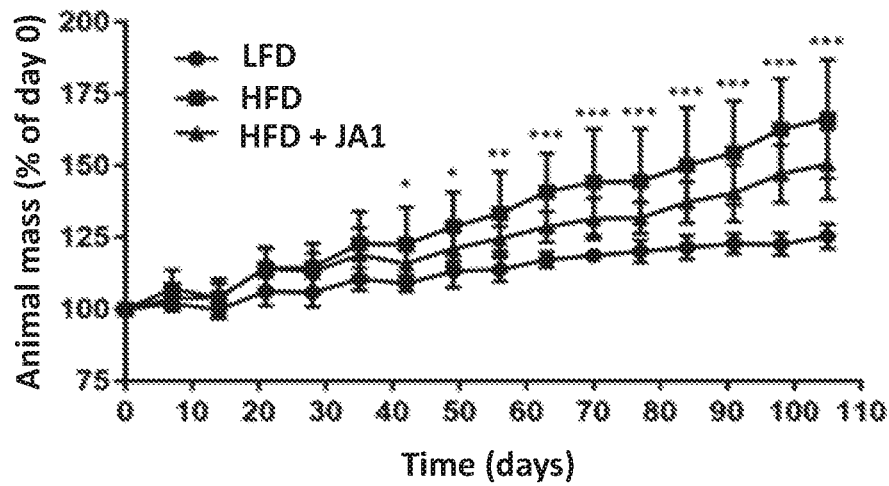
FIGS. 7A-7C show the effect of administration of *S. epidermidis* JA1 on (7A) animal mass, (7B) food consumption and (7C) gonadal adiposity at the end of the 16 week study in mice administered a high-fat diet.
Figure 7B:
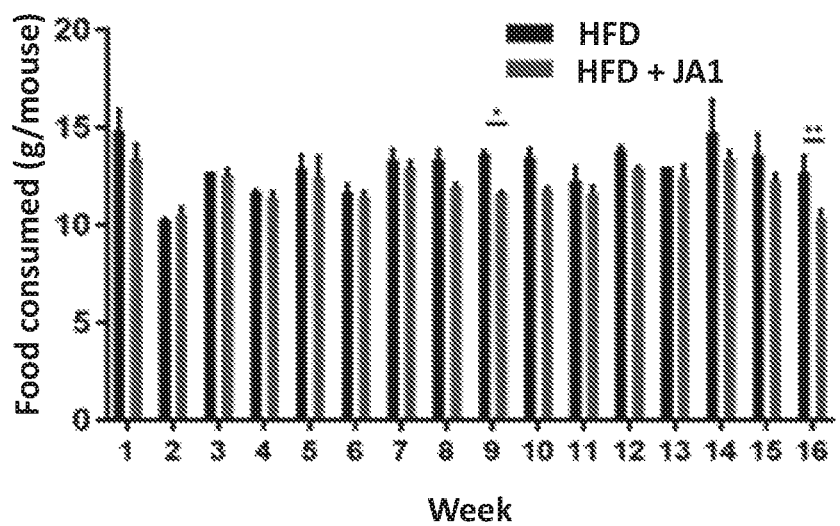
Figure 7C:
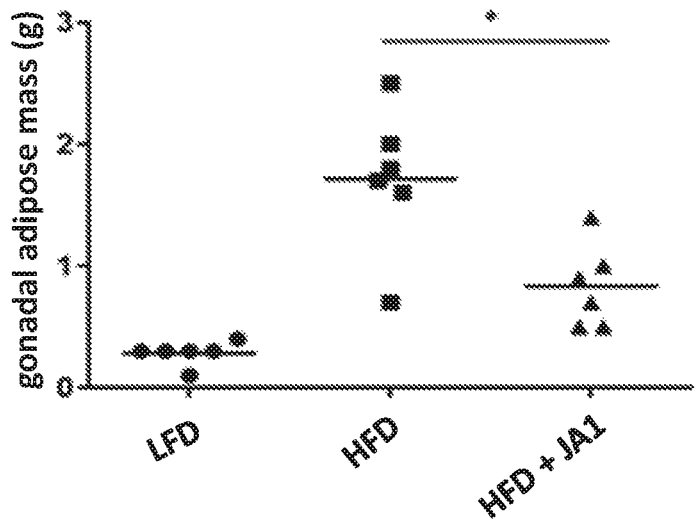

*S. epidermidis* JA1 reduces markers of metabolic disease—Following identification of JA1 as the strongest stimulator of GLP-1 secretion in vitro, its ability to modulate markers of metabolic disease was investigated using a 16 week study with C57BL/6 mice on high fat diet. Administration of *S. epidermidis* JA1 to HFD-fed mice by oral intragastric gavage for 16 weeks reduced markers of obesity, body mass and adiposity. Mice fed a HFD gained significantly more mass than mice on the conventional diet during the course of the study and mice administered JA1 significantly reduced animal mass under a HFD (FIG. 7A). This significant difference was noted as of day 42 (p=0.0423), and for the rest of the study, with animal body mass of 122.6±13.0 g and 115.9±4.7 g for the HFD-fed mice and HFD-fed mice administered JA1. As we hypothesize that *S. epidermidis* JA1 administration enhances the secretion of GLP-1, a satiety hormone, food consumption was also monitored throughout the 16 week study (FIG. 7B). The average food consumption for the HFD-fed mice was 13.0±1.15 g/week and 12.09±0.89 g/week for the HFD-fed mice administered *S. epidermidis* JA1 (p=00082), demonstrating that *S. epidermidis* JA1 reduced food intake. To assess adiposity, the gonadal adipose tissue was measured at the end of the study (FIG. 7C). Mice fed a HFD had significantly more (p<0.0001) adipose tissue mass (1.72±0.59 g) than their LFD-fed counterparts (0.28±0.10 g). Administration of *S. epidermidis* JA1 significantly reduced (p=0.004) the levels of adipose tissue mass (0.83±0.34 g).

Figure 8A:
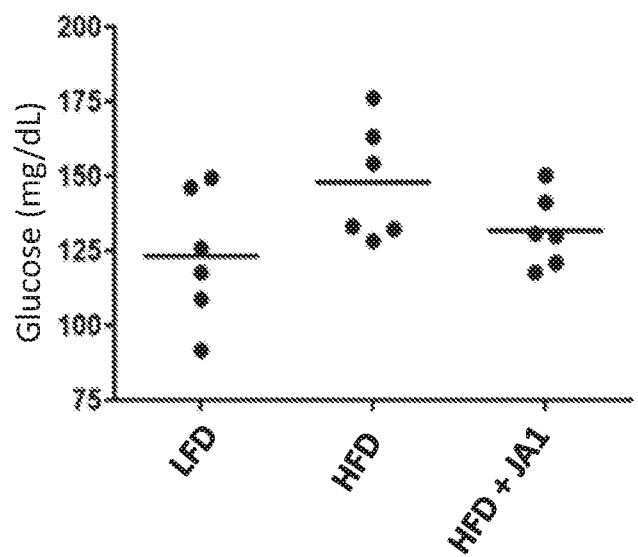
FIGS. 8A and 8B show the effect of administration of *S. epidermidis* JA1 on (8A) fasted serum glucose and (8B) fasted serum insulin levels at the end of a 16 week study.
Figure 8B:
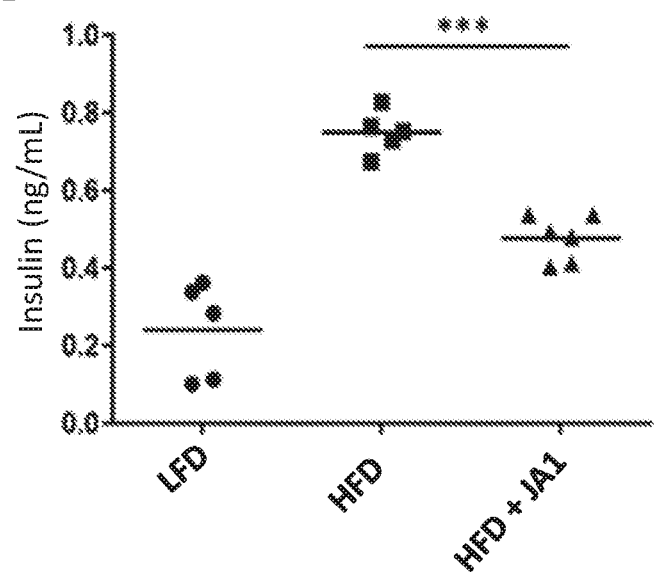

*S. epidermidis* JA1 also modulated potential markers of Type II Diabetes Mellitus, hyperglycemia and insulin resistance. HFD-fed mice had higher (147.9±19.6 mg/dL), although not statistically significant (p=0.09), fasted serum glucose levels measured at sacrifice than the LFD-fed mice (123.3±22.1 mg/dL), indicating that hyperglycemia was not developed in the model (FIG. 8A). Nonetheless, the JA1 *S. epidermidis* mice (131.8±12.2 mg/dL) trended toward having reduced fasting glucose levels when compared to the HFD-fed mice (p=0.31). Conversely, feeding with a HFD (0.75±0.06 ng/mL) significantly elevated (p<0.0001) the levels of fasted serum insulin as compared to mice administered the LFD (0.24±0.12 ng/mL) (FIG. 8B). Administration of *S. epidermidis* JA1 (0.48±0.06 ng/mL) significantly reduced (p=0.0004) fasted serum insulin levels in HFD-fed mice. Taken together, this data indicates the modulation of Type II Diabetes markers by JA1.

Figure 9:
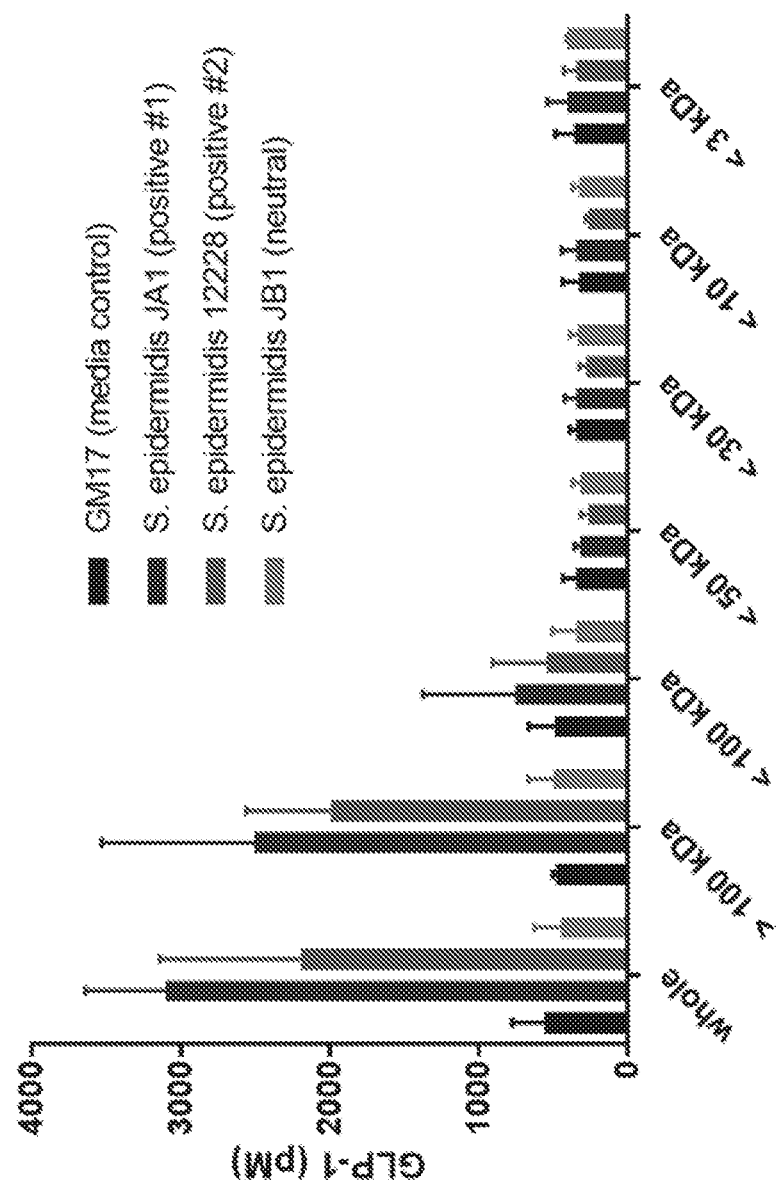
FIG. 9 shows the effect of various size fractions of *S. epidermidis* supernatants on GLP-1 secretion by NCI H716 cells. This data demonstrates that the GLP-1 stimulatory activity is present in the >100 kDa fraction.

Identifying the microbial-derived compound responsible for GLP-1 stimulatory activity—To narrow down the bacterial component responsible for GLP-1 secretion in vitro, and for metabolic disease marker modulation in vivo, size fractionation studies were performed using Amicon centrifuge filtration tubes and exposure of the fractions on NCI H716 cells. Two GLP-1 stimulatory *S. epidermidis* strains, JA1 and *S. epidermidis* type strain ATCC 12228, were used for these studies. As shown in FIG. 9, the majority of the GLP-1 stimulatory activity is present in the greater than 100 kDa fraction of the bacterial supernatants (2507±1000 pM of GLP-1 for JA1, 1998±570 pM of GLP-1 for ATCC 12228) with some remaining activity in the less than 100 kDa fraction (752±625 pM of GLP-1 for JA1, 545.3±363.5 pM of GLP-1 for ATCC 12228). It was also determined that the bacterial component is resistant to heat exposure (100° C. for 30 min) and Proteinase K treatment (50 μg/mL for 1 h) (data not shown).

Figure 10:
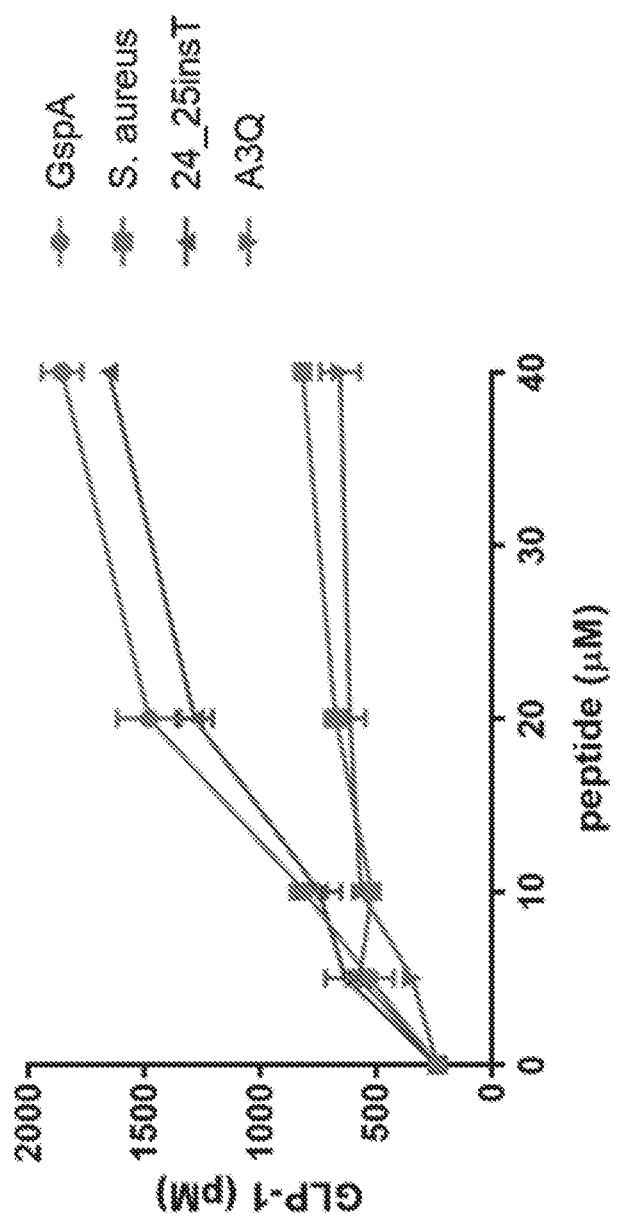
FIG. 10 shows GLP-1 stimulatory activity of GspA, *S. aureus* PsmD and the two mutants, 24_25 insT and A3Q at varying concentrations using NCI H716 cells, demonstrating activity by the GspA and 24_25 insT peptides with reduced activity by *S. aureus* PsmD and the A3Q mutant.

To further identify the component responsible for the activity, bacterial supernatants were analyzed using a Thermo Orbitrap Fusion mass spectrometer equipped with an Easy Nanospray HPLC system. Analysis of the GLP-1 stimulatory and neutral *S. epidermidis* supernatants identified 269 protein groups, of which none of these could be detected in the GM17 medium control. An excreted peptide, with amino acid sequence MAADIISTIGDLVKWI-IDTVNKFKK (SEQ ID NO:1) and a size of 3 kDa was found in the GLP-1 stimulatory *S. epidermidis* supernatants of JA1 and JA8 but absent in the GLP-1 neutral strains, JB1 and JD11. This peptide was shown to have sequence homology to a delta-hemolysin from *Staphylococcus aureus* which forms a multimeric complex in cell membranes, explaining why a 3 kDa peptide was having an activity present in the greater than 100 kDa fraction. Sequence alignment demonstrated two amino acid changes in the identified peptide as compared to *S. aureus*' delta hemolysin PsmD: 24_25insT and A3Q. Incubation of the synthesized peptide variants on NCI H716 cells demonstrated that the excreted peptide, named GLP-1 stimulating peptide A (GspA), possesses GLP-1 stimulatory activity (1481.7±137.3 pM GLP-1 with 20 μM GspA) (FIG. 10). In addition, this activity is sequence specific as it is greatly reduced in the *S. aureus* peptide PsmD (675.4±43.1 pM GLP-1 with 20 μM peptide) as well as in one of the mutants, A3Q (614.8±67.1 pM GLP-1 with 20 μM peptide). Interestingly, the 24_25insT mutant retained GLP-1 stimulatory activity (1283.5±798 pM GLP-1 with 20 μM peptide).

Figure 11A:
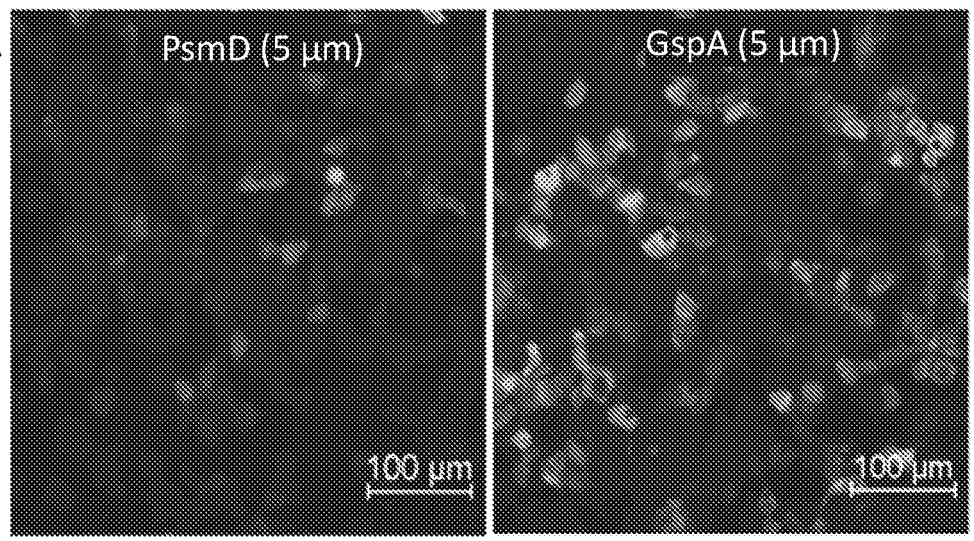
FIGS. 11A-11C show the role of GspA on calcium signalling. (11A) Fluorescence microscopy imaging of GspA on intracellular calcium flux using HEK 293 GCaMP6S cells exposed to GspA and *S. aureus* PsmD demonstrates greater intracellular calcium levels in cells exposed to GspA. (11B) Quantification of calcium flux in the HEK 293 GCaMP6S cells confirms these results. (11C) Patch clamp of NCI H716 cells exposed to GspA undergo significant cell depolarization as compared to those exposed to PsmD control peptide.
Figure 11B:
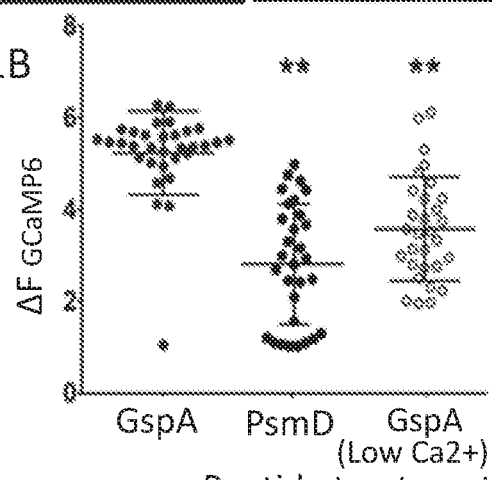
Figure 11C:
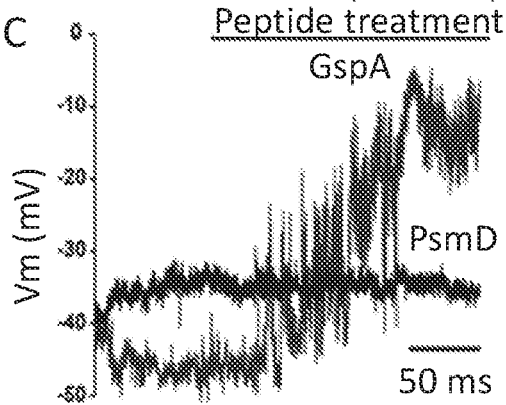

GspA can modulate intracellular calcium levels—It was considered that GspA may be stimulating the release of GLP-1 through mediation of calcium signaling, in specific embodiments. To investigate this, the inventors used HEK 293 cells expressing GCaMP6S that fluoresces green with increased intracellular calcium levels. With the HEK 293-GCaMP6S cell line GspA was shown to increase levels of cytoplasmic calcium, as shown by the increased green fluorescence signal following exposure to the peptide (FIG. 11A). The increase with GspA was significantly greater than PsmD and was also attenuated by EDTA chelation of extracellular calcium, suggesting influx as the primary source of calcium ions (FIG. 11B). In addition, electrophysiology studies were performed using patch clamp to measure ionic currents that would be impacted by calcium signaling changes. GspA does cause a significant depolarization of NCI H716 cells while PsmD did not demonstrate this depolarization activity (FIG. 11C). Taken together, this data indicates that in specific embodiments GspA is stimulating GLP-1 release via a calcium-dependent mechanism.

Figure 12B:
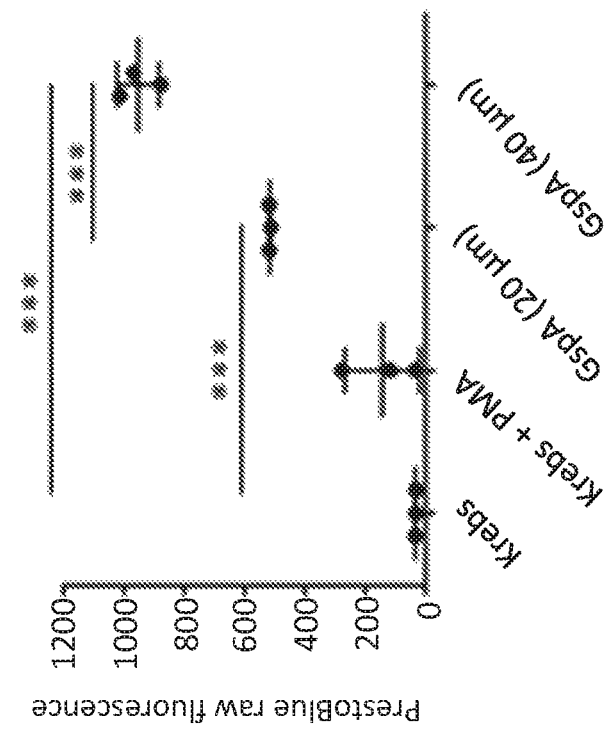
FIGS. 12A-12F show GspA exposure on neurogen-3 transduced human intestinal enteroids. It demonstrates specificity in its activity. GspA exposure did not lead to a loss of (12A) cell viability as determined by a resazurin-based PrestoBlue assay. GspA did enhance the secretion of (12B) GLP-1 and (2C) serotonin but not (12D) glucagon, (12E) Peptide-YY and (12F) gastric inhibitory peptide.
Figure 12A:
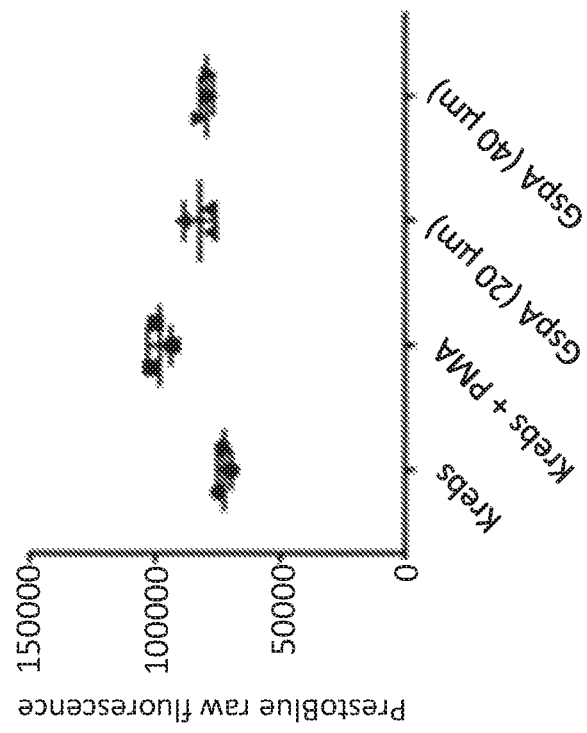
Figure 12C:
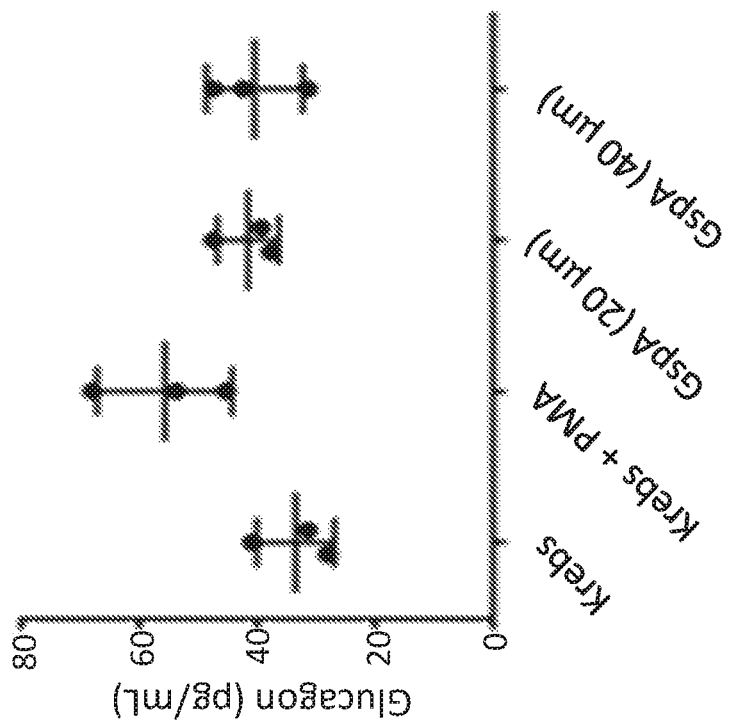
Figure 12D:
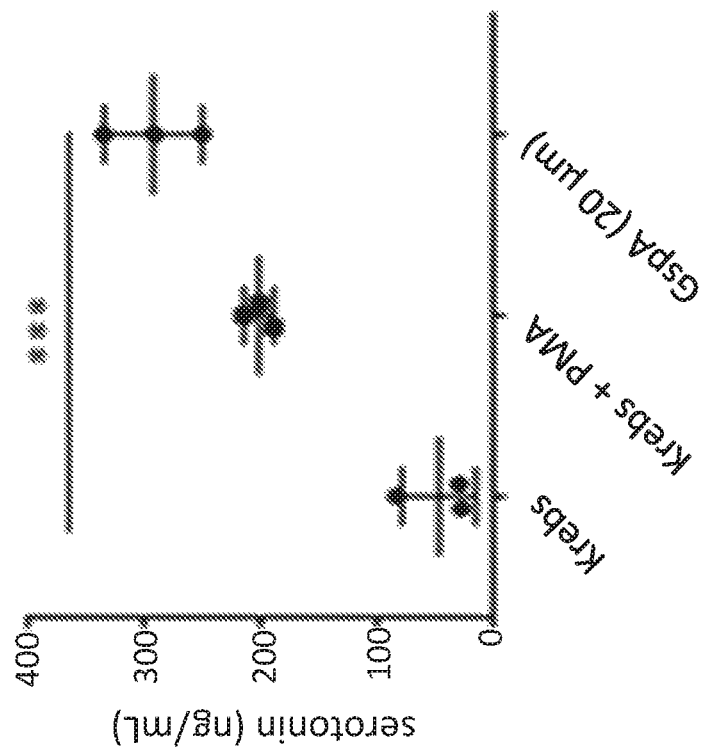
Figure 12F:
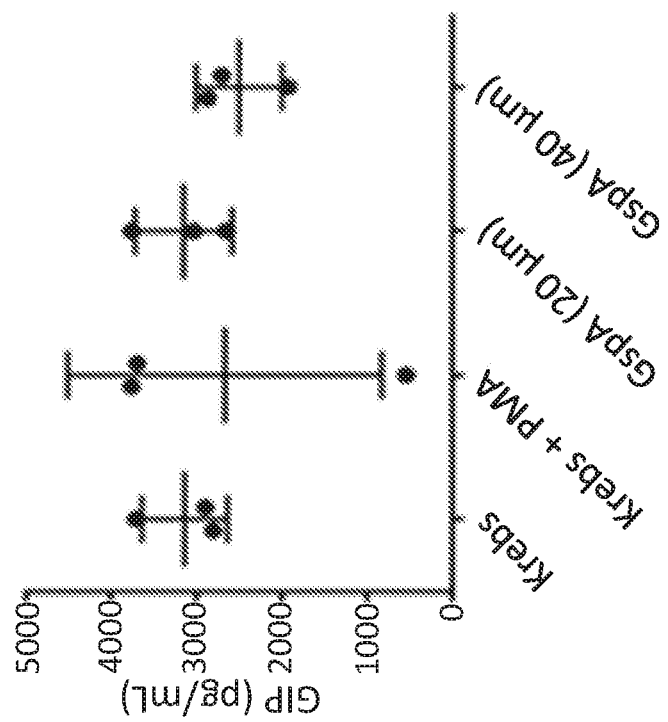
Figure 12E:
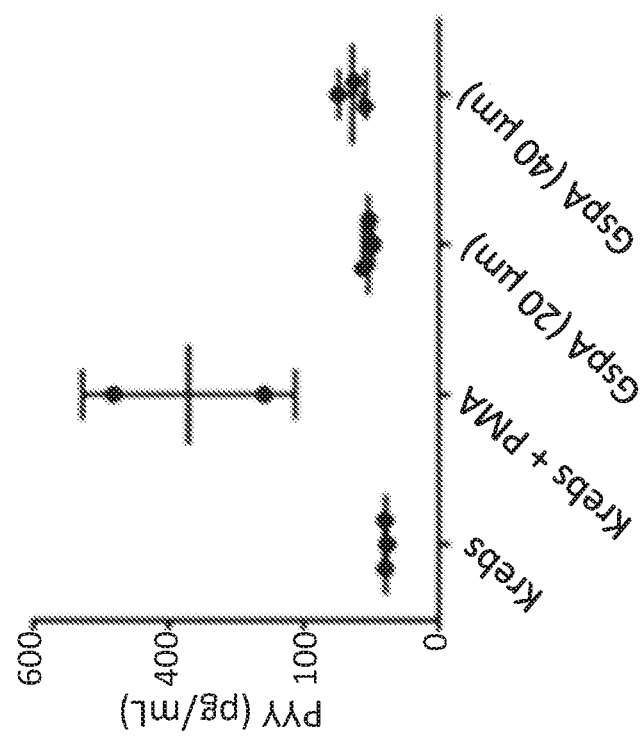

GspA's activity demonstrates specificity—It was investigated whether GspA was simply making holes in cell membranes, causing the release of GLP-1, and also what other molecules were released by GspA exposure. Using neurogenin-3 (a transcription factor that stimulates enteroendocrine cell differentiation, giving rise to higher enteroendocrine cell counts and GLP-1 levels), the specificity of GspA was demonstrated. Following exposure to GspA, there was no visible effect on cell viability, as measured by a PrestoBlue resazurin based assay (FIG. 12A), indicating that GspA is not simply lysing the cells. This is supported by the earlier data showing no toxicity in NCI H716 and GLUTag cells. As validation of the GLUTag and NCI H716 GLP-1 data, GspA did indeed enhance GLP-1 secretion in the enteroid model (FIG. 12B). Interestingly, GspA exposure also stimulated the release of another gastrointestinal molecule, serotonin (FIG. 12C). Conversely, GspA did not stimulate the release of glucagon (FIG. 12D), peptide YY (FIG. 12E) or gastric inhibitory peptide (FIG. 12F). Taken together, this data indicates specificity in GspA's mechanism of action for the release of gastrointestinal hormones, not simply as a non-specific pore-forming complex.

What is claimed is:

1. A method of treating a medical condition in an individual having insufficient levels of glucagon-like peptide-1 (GLP-1), comprising the step of administering to the individual a therapeutically effective amount of a peptide comprising MAADIISTIGDLVKWIIDTVNKFKK (SEQ ID NO:1), or a functionally active fragment or derivative thereof; wherein the functionally active fragment comprises at least the amino acids between, and including, positions 3-24 of SEQ ID NO:1; wherein the derivative comprises only conservative amino acid substitutions to SEQ ID NO:1, wherein the medical condition is obesity, type II diabetes, being overweight, Metabolic syndrome, Non-alcoholic fatty liver disease (NAFLD), short bowel syndrome, or a combination thereof.

2. The method of claim 1, wherein the individual is administered another therapy for the medical condition.

3. The method of claim 1, further comprising the step of determining the level of GLP-1 in the individual, wherein the therapeutically effective amount depends on the level of GLP-1 in the individual.

4. The method of claim 1, wherein the peptide consists of the sequence of SEQ ID NO:1.

5. The method of claim 1, wherein the peptide consists essentially of the sequence of SEQ ID NO:1.

6. The method of claim 1, wherein the sequence of the derivative is at least 85, 90, or 99% identical to the sequence in SEQ ID NO: 1.

7. A method of treating a medical condition in an individual having insufficient levels of glucagon-like peptide-1 (GLP-1), comprising the step of administering to the individual a therapeutically effective amount of a peptide comprising MAADIISTIGDLVKWIIDTVNKFKK (SEQ ID NO:1), or a derivative thereof; wherein the derivative comprises only conservative amino acid changes to SEQ ID NO: 1 and does not have an alteration in the underlined positions of SEQ ID NO: 1 as follows: MA<u>A</u>DIISTIGD- LVKWI-IDTVNKF<u>K</u>K, wherein the medical condition is obesity, type II diabetes, being overweight, Metabolic syndrome, Non-alcoholic fatty liver disease (NAFLD), short bowel syndrome, or a combination thereof.

\* \* \* \* \*

UNITED STATES PATENT AND TRADEMARK OFFICE
CERTIFICATE OF CORRECTION

PATENT NO. : 11,028,141 B2  
APPLICATION NO. : 16/348443  
DATED : June 8, 2021  
INVENTOR(S) : Robert Allen Britton et al.

Page 1 of 1

It is certified that error appears in the above-identified patent and that said Letters Patent is hereby corrected as shown below:

In the Claims

In Claim 7:
At Column 21, Line numbers 9-10, delete within SEQ ID NO: 1 "MA<u>A</u>DIISTIGD LVKWI IDTVNKF<u>K</u>K" and replace with "MA<u>A</u>DIISTIGDLVKWIIDTVNKF<u>K</u>K"

Signed and Sealed this  
Twenty-ninth Day of March, 2022

Drew Hirshfeld  
*Performing the Functions and Duties of the*  
*Under Secretary of Commerce for Intellectual Property and*  
*Director of the United States Patent and Trademark Office*